United States Patent
Jewell

(10) Patent No.: US 9,161,870 B2
(45) Date of Patent: Oct. 20, 2015

(54) HEEL SUPPORT FOR MULTIPLE PATIENT ORIENTATIONS

(75) Inventor: Gwen Jewell, San Carlos, CA (US)

(73) Assignee: Gwen Jewell, San Carlos, CA (US)

(*) Notice: Subject to any disclaimer, the term of this patent is extended or adjusted under 35 U.S.C. 154(b) by 587 days.

(21) Appl. No.: 13/432,268

(22) Filed: Mar. 28, 2012

(65) Prior Publication Data

US 2012/0247484 A1  Oct. 4, 2012

Related U.S. Application Data

(60) Provisional application No. 61/471,500, filed on Apr. 4, 2011.

(51) Int. Cl.
*A47C 20/04* (2006.01)
*A61G 7/075* (2006.01)
*A61F 13/06* (2006.01)
*A61G 7/057* (2006.01)

(52) U.S. Cl.
CPC .............. *A61G 7/075* (2013.01); *A61F 13/069* (2013.01); *A61G 7/057* (2013.01); *A61G 7/05723* (2013.01); *A61G 7/0755* (2013.01); *A61G 2200/32* (2013.01); *A61G 2200/56* (2013.01)

(58) Field of Classification Search
CPC ..... A61F 13/06; A61F 13/064; A61F 13/069; A47C 20/00; A47C 20/02; A47C 20/021; A47C 20/022; A61G 7/0755; A61G 2200/32; A61G 2200/56; A61G 7/075; A61G 7/025723; A61G 7/057
USPC .............. 128/845, 889, 892; 5/649, 651, 648, 5/650

See application file for complete search history.

(56) References Cited

U.S. PATENT DOCUMENTS

| | | | | |
|---|---|---|---|---|
| 2,782,427 | A * | 2/1957 | Ericson | 5/632 |
| 2,933,738 | A * | 4/1960 | Whelan | 5/630 |
| 3,931,654 | A * | 1/1976 | Spann | 5/327 |
| 4,067,330 | A * | 1/1978 | Roache | A61F 15/006 128/889 |
| 4,482,138 | A * | 11/1984 | Spann | 5/648 |
| D393,071 | S * | 3/1998 | Kennemore | D24/183 |
| 5,790,998 | A * | 8/1998 | Crescimbeni | 5/648 |
| 5,882,324 | A * | 3/1999 | Baranowski | 602/65 |
| 6,076,213 | A * | 6/2000 | Chase, Jr. | 5/706 |
| 6,371,894 | B1 * | 4/2002 | Hill | 482/121 |
| 6,634,045 | B1 | 10/2003 | DuDonis et al. | |
| D683,031 | S * | 5/2013 | Du | D24/183 |

* cited by examiner

*Primary Examiner* — Tatyana Zalukaeva
*Assistant Examiner* — Camtu Nguyen
(74) *Attorney, Agent, or Firm* — Convergent Law Group LLP; Rick Batt

(57) ABSTRACT

A heel support for elevating the heel and bony prominences of a patient's lower limbs in multiple patient orientations. The heel support includes a plurality of apertures for floating the ankles and bony prominences when the patient is positioned on her side. The heel support additionally includes one or more edge contours for floating the heel and boney prominences of the foot when the patient is positioned on her back. The heel support has a size and shape which makes it comfortable to the patient whether the patient is on her back or side. The heel support is portable and convenient to manipulate for hospital staff. A washable or disposable cover may be provided.

17 Claims, 7 Drawing Sheets

HEEL SUPPORT FOR MULTIPLE PATIENT ORIENTATIONS

CROSS-REFERENCE TO RELATED APPLICATIONS

This claims the benefit of provisional patent application No. 61/471,500, filed Apr. 4, 2011.

BACKGROUND OF THE INVENTION

A common problem facing bedbound people is decubitus ulcers otherwise known as pressure sores. A pressure sore can occur whenever a bony prominence of a person is subjected to unrelieved pressure. This pressure causes reduced circulation and eventual skin breakdown. An ulcer can occur in as little as a few hours if conditions are right. The sore(s) will start with what appears to be a simple bruise, but if pressure is unrelieved, it can lead to a sore that can go deep into the soft tissue, and if not adequately addressed, the pressure will cause the sore to open all the way to the bone.

Persons who are bed bound or chair bound, have compromised skin integrity due to poor health, and/or is desensitized from anesthesia, pain medication or neurological impairment, are prone to pressure ulcers. It is a common occurrence in the hospital setting, especially for those in long term care and those who are subject to long operations in where they are not moving naturally. Hospital management has a strong incentive to prevent such sores and the infections that may arise there from, as they can be costly for all involved.

The most common spots for pressure sores are the heel of the feet and the sacral/coccyx area of the lower back, because these spots are difficult to support without pressure and there is only a thin layer of skin over these bony prominences. To minimize the pressure to the lower back, the care giver must shift the patient frequently by "turning" them from side to side so that they do not stay on any one pressure point for an extended time. As for the feet, the standard of care is to "float" the heels off the surface of the bed by tucking pillows under the persons lower legs so that the heels do not touch anything.

Standard pillows and foam wedges have been used to "float" the heels off the surface of the bed. However the use of standard pillows and known foam wedges to float the heels suffer from a number of problems.

Standard pillows, although soft and malleable making it easy for a care giver to "shape" the pillows so that they can accomplish "floating", are inadequate for the long term because the soft pillows cannot hold the shape the care giver fashioned. Additionally, the pillows tend to slip out of place or "bottom out" under the weight and natural shifting of the patients' movements. Frequently one will find direct pressure from the pillow itself only a few minutes after it had been "shaped" to do the opposite. Thus a standard pillow is not an effective tool to prevent pressure sores of the heel.

Another approach is to use a specially shaped foam wedge to support the lower legs. Foam wedges have an advantage over a soft pillow because the foam material maintains a specific shape, and it will not easily move out of place with shifting of the patient. A number of heel supporting wedges are available and most have a square shape, with a thickness high enough to elevate the heel well above the bed. Some of the foam wedges are shaped with a sloping angle so as to provide support under the knees and thighs.

Although these wedges serve to elevate the feet, often well above the heart, they have a number of shortcomings.

First, these types of wedges are too thick. Although the heel floating wedges available now can accomplish an elevation of the entire lower limb, they are well over 12" thick. The wedges are so high that the wedge must be removed when the patient is turned to their side, which should occur at least every 2 hours. If the patient were to have a wedge this large under her body when on her side, her lower back/hips would be so twisted as to cause injury.

Another problem with the known foam wedges is the existence of long square edges. There are many patients who are not able to extend their legs to a full straight position due to musculoskeletal malformations, and thus cannot get a thick wedge all the way under their legs. Because of the solid shape of the wedge, if one limb is shorter than the other, only one heel can be floated. Square edges tend to be effective only when the patients' foot is angled at 90 degrees from the edge, which is not always a natural or comfortable position.

Another problem with the known foam wedges is that they address only floating the heels. Even if the patient could tolerate the wedge under the legs while on the side, the bony prominence of the ankles, the lateral and proximal malleolus, and of the feet, the medial and lateral sides of the phalanges, which are also common sites for pressure sores, are subject to pressure unless the entire foot was suspended off the wedge. Floating the entire foot causes a transfer of weight uncomfortable to the ankle joint, putting undue stress on the ankle and subsequent injury.

Another problem with the known foam wedges is that they are too big. Wedges tend to be bulky and cumbersome, making them awkward for a care giver to position, and for a hospital to store when not in use. Many are designed to support the entire lower limb up to the patient's buttocks. They can impede with the care of the patient during cleaning and are susceptible to soiling. Contrary to hospital pillows, they cannot be covered easily with a standard pillow case, so when soiled, they cannot simply remove the pillowcase and throw it in the laundry then wipe it down as they do with pillows. Indeed, a large wedge is difficult and inconvenient to rinse off under a running faucet. These factors are enough to discourage a rushed caregiver to use the known foam wedges.

There have been attempts to address some of the above shortcomings. An example of a foam cushion which addresses some of the above described shortcomings is disclosed in U.S. Pat. No. 6,634,045 to DuDonis and shown in FIG. 1.

However, despite the availability of some of the known pillows and foam wedges, a heel support for floating the heels from the bed in multiple patient orientations and without the above identified problems is still desired.

SUMMARY OF THE INVENTION

The present invention is a heel support for elevating the heel of a patient from a bed when the patient is positioned on her back. In one embodiment, the heel support elevates the heel of a patient from a bed when the patient is positioned on her back and floats the malleolus and bony sides of the foot phalanges when the patient is positioned on her side. In one embodiment the heel support includes a body member having an upper surface, a left edge, a right edge, and a distal edge. The distal edge has a first contour such that when the patient is on her back and the support is positioned underneath the patient's legs, the support acts to maintain the legs of the patient on the support and to float the heels of the patient from the bed. The first contour may have a concave shape.

In another embodiment the heel support includes a right side malleolus aperture located in a distal region of the support and having a shape sufficient to accommodate the lateral malleolus and heel of the patient's right leg when the patient is positioned on her right side and the support is positioned underneath the legs of the patient.

In another embodiment the heel support comprises a left side malleolus aperture located in the distal region of the support and having a shape sufficient to accommodate the medial malleolus of the patient's left leg when the patient is positioned on her right side and the support is positioned underneath the legs of the patient.

The left edge of the heel support may comprise a second contour shaped such that when the patient is on her right side, and the malleolus of the left leg is disposed in the left side malleolus aperture, the heel of the left leg extends off of the left side of the support, floating from the bed. The second contour may have a concave shape.

In another embodiment the heel support includes a proximal region and a distal region wherein the proximal region of the support is substantially planar and forms an angle with the distal region of the support. The angle may range from 1 to 10 degrees, or more preferably 3 to 7 degrees. In one embodiment the angle is about 5 degrees. The angle accommodates the natural bend under the patient's knees when she is positioned on her back.

In another embodiment the heel support includes a third aperture in the distal region of the support. The third aperture is centrally located and for accommodating bony prominences of the feet when the patient is positioned on her side.

In another embodiment the malleolus aperture extends completely through the support.

In another embodiment the heel support includes a knee-length hip-width substantially flat body, and a distal edge contour adapted to float the heels of the patient and to urge the legs to remain on the support when the patient is on her back. The heel support includes a plurality of malleolus apertures located in a distal zone of the support and adapted to float the left ankle malleolus and the right ankle malleolus when the patient is on her side.

The heel support is generally thick enough to float the heel, but thin enough to allow use and accomplish floating while the patient is on her side. In one embodiment, the heel support has a foot end height and a torso end height wherein the foot end height is greater than the torso end height and the foot end height being sufficient to elevate the heel of the patient when the patient is on her back and low enough to allow the support to be comfortably positioned underneath the patient's legs when the patient is on her side. The height of the heel support at the foot end may range from 2 to 4 inches. The foot end is about 3.25 inches thick in one embodiment.

In another embodiment the heel support has a maximum width in the range of 15 to 25 inches and in one embodiment has a maximum width of approximately 21 inches. In another embodiment the heel support has a maximum length in the range of 15 to 25 inches and in one embodiment has a maximum length of approximately 21 inches. In another embodiment the heel support has a minor length equal to the distance from the patient's knee to her ankle. The support is not as subject to soiling.

In another embodiment the heel support has a size such that it can fit in a pillowcase, making it easy to use and store, and not bulky.

In another embodiment the heel support has multiple contoured edges so that regardless of how the patient naturally positions their legs, the support will still accomplish bony prominence floating. The heel support is contoured at the edges and has holes under the boney prominences allowing for floating of all the boney prominences while supporting the ankles.

In another embodiment the heel support has at least one handle or aperture.

In another embodiment the heel support is covered with a dis-infectable, moisture resistance surface that is a high grade, breathable vinyl or nylon designed especially for medical use called Nylex. The cover may also be made of a soft cotton material. The cover may be removable. The cover may be made of a washable or disposable material.

In another embodiment the body of the heel support is formed of a plurality of layers including a top layer. The top layer may be formed of a memory foam.

In another embodiment the heel support comprises three or more layers (e.g., foam layers). An inner or middle layer is sandwiched between outer layers. The inner layer or layers may comprise holes or cut-outs. In one embodiment the body comprises one or more enclosed cavities. The holes and cut-outs may have shapes and locations as described herein. The assembled support may then be covered with a removable or non-removable cover.

In another embodiment, the heel support comprises a shape as shown in any one of the figures disclosed herein.

The description, objects and advantages of the present invention will become apparent from the detailed description to follow, together with the accompanying drawings.

DETAILED DESCRIPTION OF THE INVENTION

Figure 1:
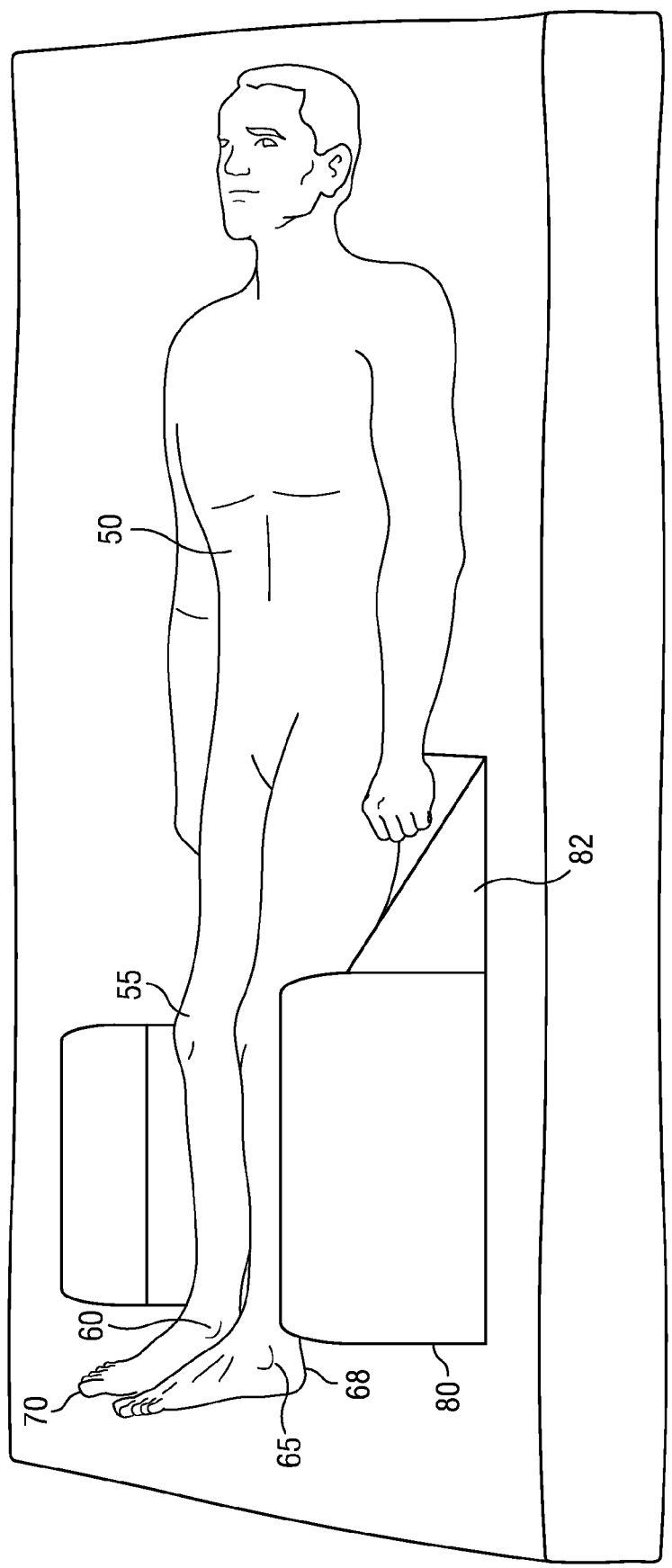
FIG. 1 shows a perspective view of a prior art heel elevator support in use.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The present invention is directed to a heel support for elevating the heel and bony prominences of a patient's lower limbs in multiple patient orientations. The heel support is adapted to float the heel and bony prominences of the foot and ankle whether the patient is on her back or sides. By "float", it is meant that the anatomical feature does not make contact with the bed or the support. Consequently, as described above, pressure sores amongst other things may be inhibited or prevented or able to heal.

With reference to FIGS. 2A-2D, a heel support 110 in accordance with one embodiment of the present invention is shown. The support shown in FIGS. 2A-2D includes a distal or foot end edge 112, a proximal or torso end edge 114, a left side edge 118A, a right side edge 118B, and an upper surface or top surface 116.

The upper surface 116 is shown having regions or zones. In particular, the support is shown divided into a proximal zone 113 and a distal zone 111. In the embodiment shown in FIG. 2B, the proximal or torso zone 113 forms an angle α with distal section or zone 111. The angle α may vary widely and in one embodiment it ranges from 1 to 10 degrees and more preferably about 3 to 7 degrees. However, as described herein, the upper surface need not comprise sloped or inclined zones.

Figure 2A:
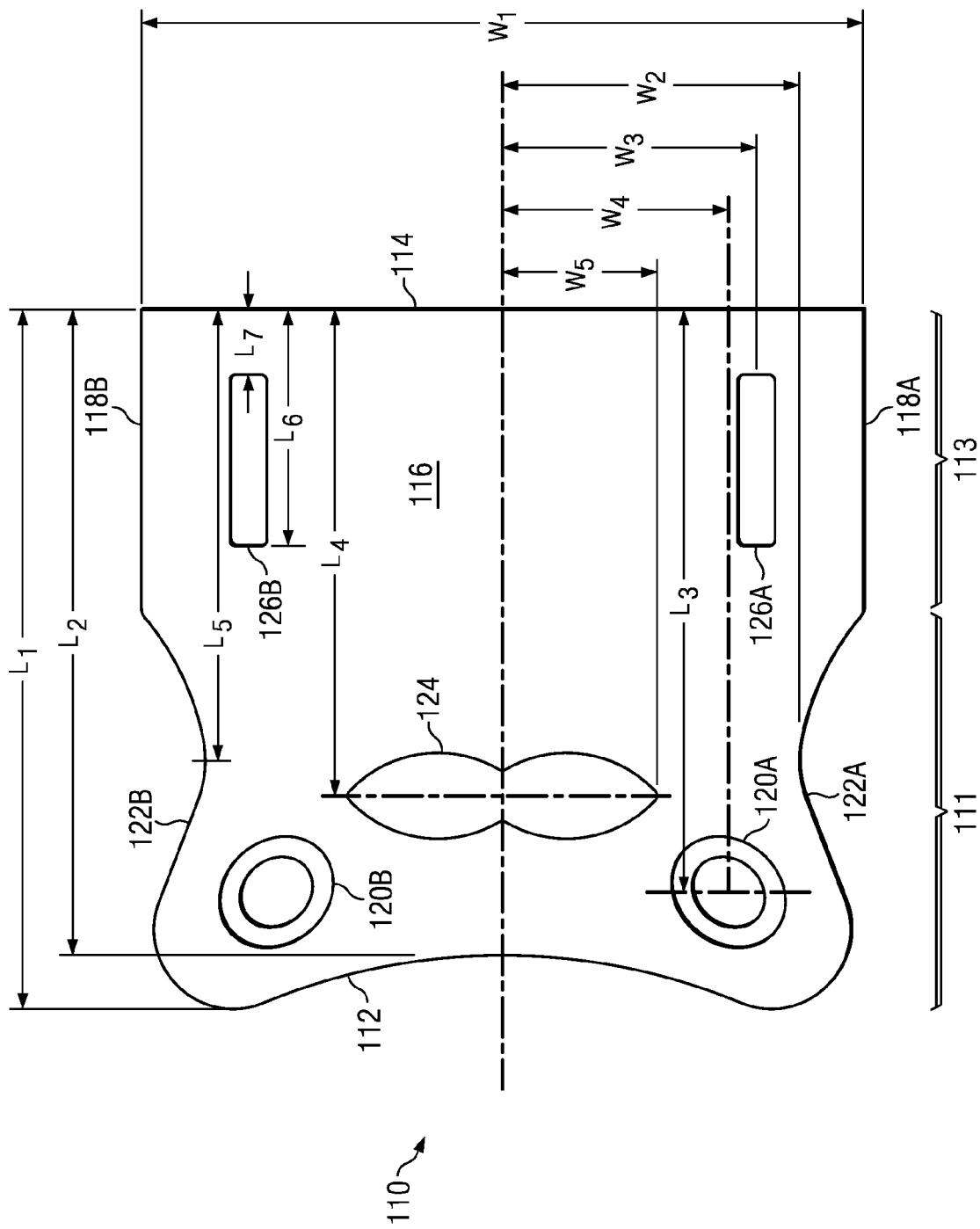
FIG. 2A shows a top view of a heel support in accordance with a first embodiment of the present invention.
Figure 2B:
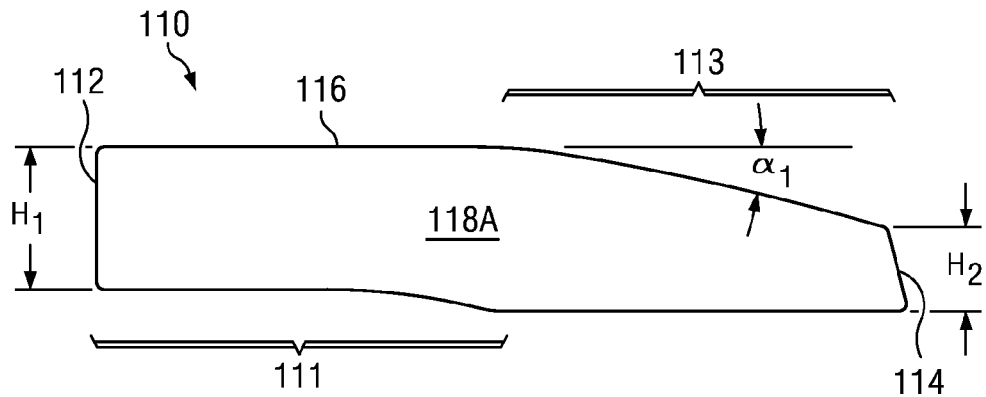
FIG. 2B shows a left side view of the heel support shown in FIG. 2A.
Figure 2C:
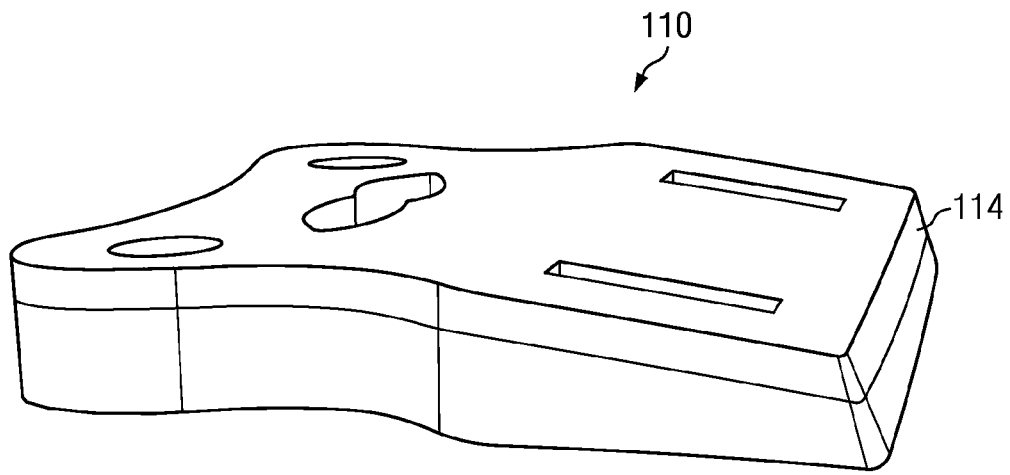
FIGS. 2C and 2D show perspective views of the heel support shown in FIG. 2A
Figure 2D:
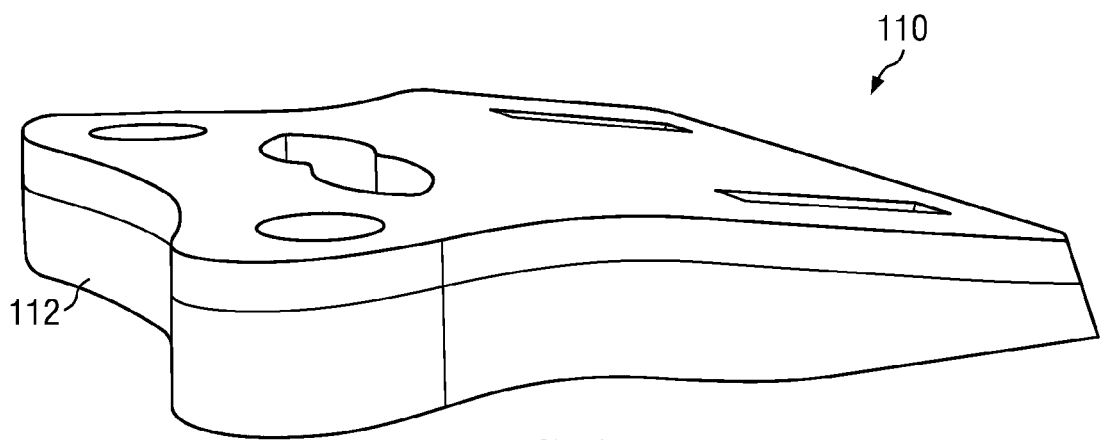

The heel support shown in FIGS. 2A-2D includes a plurality of apertures and contours for elevating and floating the boney prominences of the patient's lower limbs. In particular, with reference to FIG. 2A, support 110 includes a set of malleolus apertures 120A, 120B for supporting the malleolus and boney prominences of the foot as will be described in more detail below in connection with FIGS. 4A-4B. The malleolus apertures are located in the distal zone 111 and in the variation shown in FIG. 2A, are located a distance W4 in the range of 3 to 8 inches from the center line CL and a distance L3 in the range of 12 to 17 inches from the proximal edge 114. Malleolus apertures 120A, 120B have a diameter suitable for circumscribing a malleolus and range from 2 to 5 inches. The apertures 120A and 120B can have various shapes, and preferably are round or oval. A centrally located aperture 124 for supporting the boney prominences of the foot and ankle is also shown in FIGS. 2A-2D. Centrally located aperture 124 is shown having a thin wide oval shape.

Handle apertures 126A and 126B are also shown in FIG. 2A. It should be understood, however, that the invention is only to be limited as recited in the appended claims and may include more or less apertures and features. Additionally, the use of the term "aperture" is meant to include apertures that extend completely through the support as well as those that do not extend completely through the support. By way of non-limiting example, "aperture" is meant to include a through-hole as well as a cavity, pit or recess.

The size of the heel support 110 may vary. Generally but not necessarily, however, the length and width of the support are preferably sufficient to fit in a pillow case. In one embodiment, the length and width are approximately equal to the distance between the ankle and the knee of an average sized adult.

More preferably, and with reference to FIG. 2A, each of the length L1 and width W1 may range from 15-25 inches, more preferably 20 to 22 inches, and most preferably approximately 21 inches. Though the width and length are shown equal to one another in FIG. 2A, they need not be equal. Indeed, the length may be equal to, greater, or less than the width of the heel support.

The height or thickness of the support of the present invention may vary. Preferably the heel support is thick enough to float the heel, but thin enough to accomplish floating while the patient is comfortably positioned on her side. Thus, the upper limit of the height must be tailored to meet the constraint that the patient may utilize the support on her side. With reference to the embodiment shown in FIG. 2B, the torso end height H2 may range from 1 to 4 inches, and more preferably is about 2 to 3 inches. In one embodiment the torso end height is 2.25 inches. The height of the heel support at the foot end H1 ranges from 2 to 6 inches, more preferably 2 to 4 inches, and in one embodiment the height at the foot end is approximately 3.25 inches. In another embodiment, the height is substantially constant, and ranges from 3 to 4 inches.

In use, the heel support of the present invention may serve to support a patient in multiple patient orientations, namely, her back and sides.

Figure 3A:
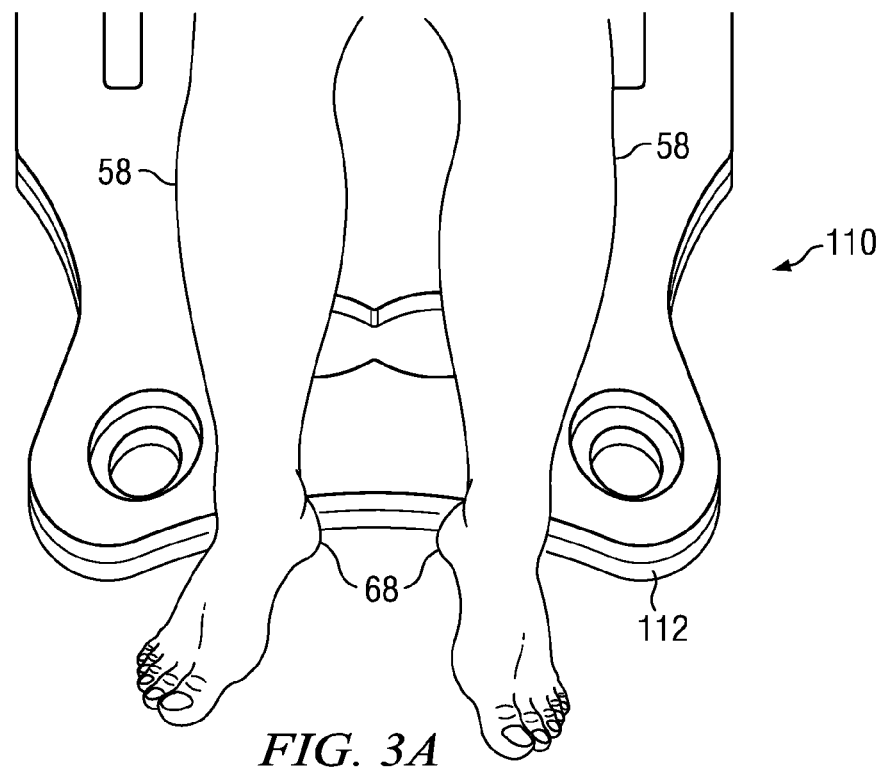
FIGS. 3A and 3B show a top view and a right side view respectively of the heel support of FIG. 2A in a first use, namely, wherein the patient is positioned on her back.
Figure 3B:
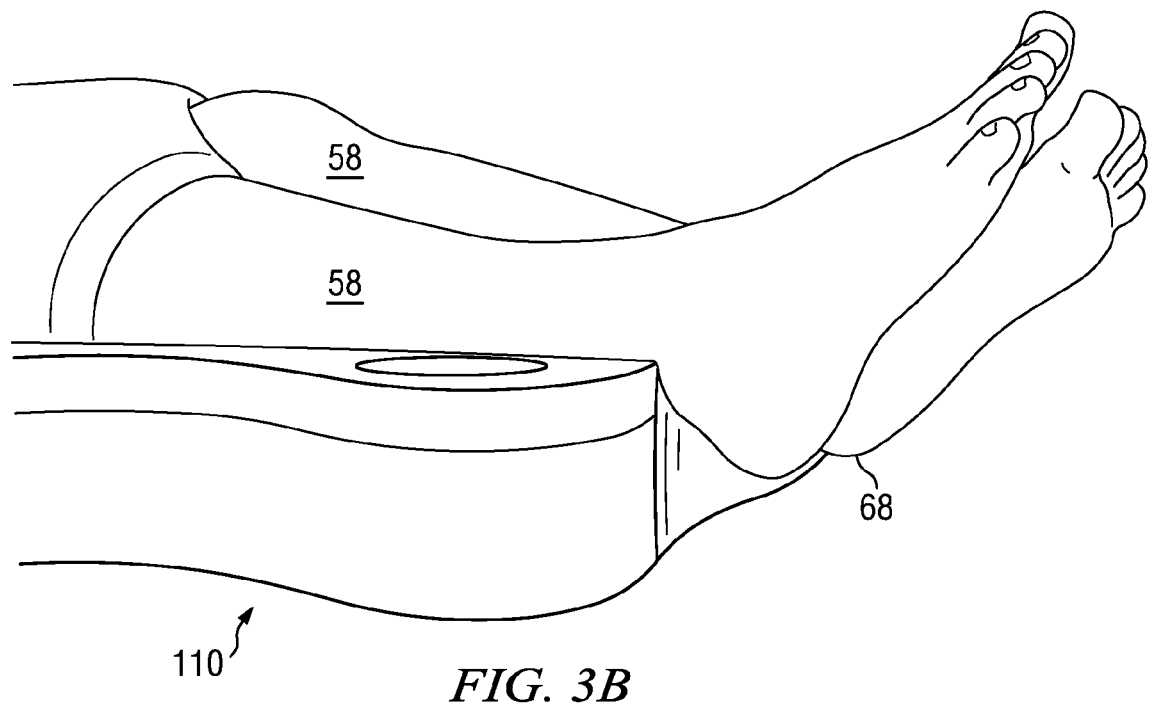

With reference to FIGS. 3A-3B, a partial view of the heel support 110 and a patient on her back is shown. The support 110 is shown positioned underneath the patient's legs 58 such that the heels 68 are elevated from the bed or floated. Distal edge 112 features a contour adapted to float the feet, allow space between the feet, and to remain on the support 110. The contour 112 shown in FIG. 3A includes a curve and in particular, shows a concave edge. The valley of edge is located along the center line CL at a distance L2 ranging 17 to 19 inches from the proximal edge. It should be understood however, that the invention may include other contours curved or otherwise and the invention is only intended to be limited as recited in the claims herein appended.

Figure 4A:
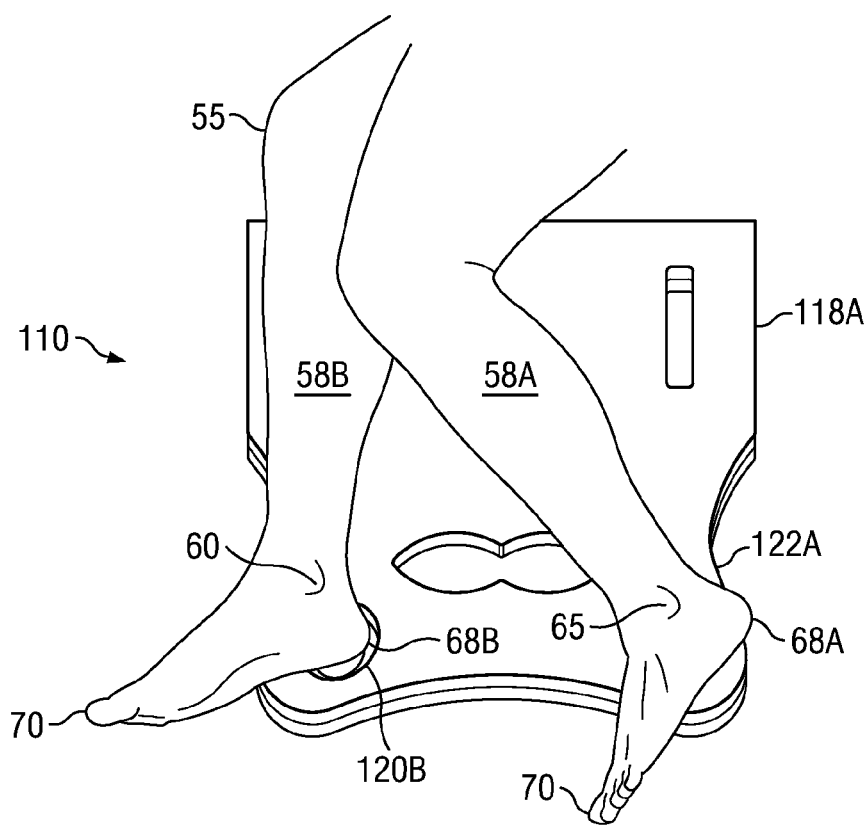
FIGS. 4A and 4B show a top view and a right side view respectively of the heel support of FIG. 2A in a second use, namely, wherein the patient is positioned on her right side.
Figure 4B:
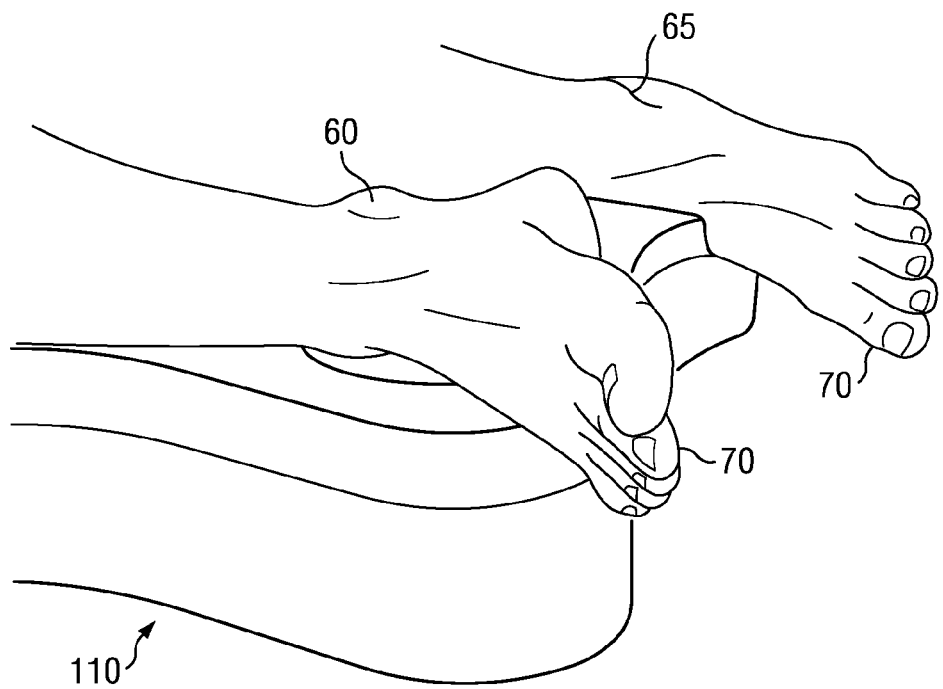

With reference to FIGS. 4A-4B, a partial view of the heel support 110 and a patient on her right side is shown. The heel support 110 is shown positioned underneath the patient's legs 58A, 58B such that the patient's ankle bones, malleolus, and heels are elevated from the bed or floated. In particular, the medial malleolus of the left leg is floated over left side aperture 120A and the lateral malleolus and heel bones of the right leg are floated over right side aperture 120B. Additionally, the left edge 118A includes a contour 122A which enables the heel bone prominences of the left leg to float above the bed. The contour shown in FIG. 4A is concave. The concave valley is located a distance W2 ranging 7 to 10 inches from the CL and a distance L5 ranging 11 to 14 inches from the proximal edge 114. As shown in FIG. 4A, the heel 68A of the left lower limb 58A extends over the left side edge of the support serving to float the heel while at the same time supporting the ankle joint, preventing bed sores and/or joint stress from arising.

Figure 5:
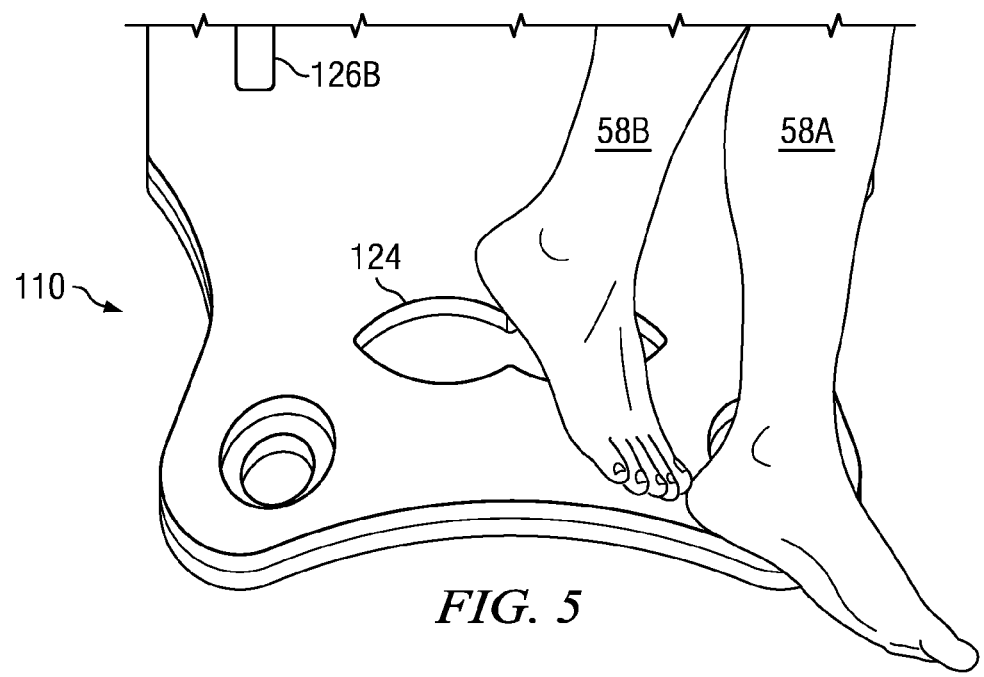
FIG. 5 shows a partial top view of the heel support of FIG. 2A in a third use, namely, wherein the patient is positioned on her left side.

FIG. 5 shows a partial top view of the heel support of FIG. 2A in a third use, namely, wherein the patient is positioned on her left side. The use demonstrated in this figure illustrates the right leg 58B resting on the support 110 with boney prominences and the medial malleolus floating over central aperture 124. Central aperture 124 is positioned in distal region or zone 111 along the centerline CL. In the embodiment shown in FIG. 2A, aperture 124 is a distance L4 ranging from 10 to 17 inches from the proximal edge 114 and has a radius or half width W5 ranging from 3.5 to 6 inches (or full width of 7 to 12 inches). Thus, when the patient is in a side orientation, the support 110 allows for multiple leg configurations or positions.

FIG. 5 additionally shows handle aperture 126B for carrying support 110. The handle is shown having a distance (W3) of 7 to 9 inches from the center line and a distance L7 of 2.5 to 4.5 inches from the proximal edge 114. The handle preferably has length of about 1 to 6 inches. However, the handle aperture size and location may vary. Another variation of the invention is to attach a handle to the body of the support. For example a soft cloth or leather strip may serve as a handle fastened to the body of the support. A cover may be provided which includes the handle.

Figure 6:
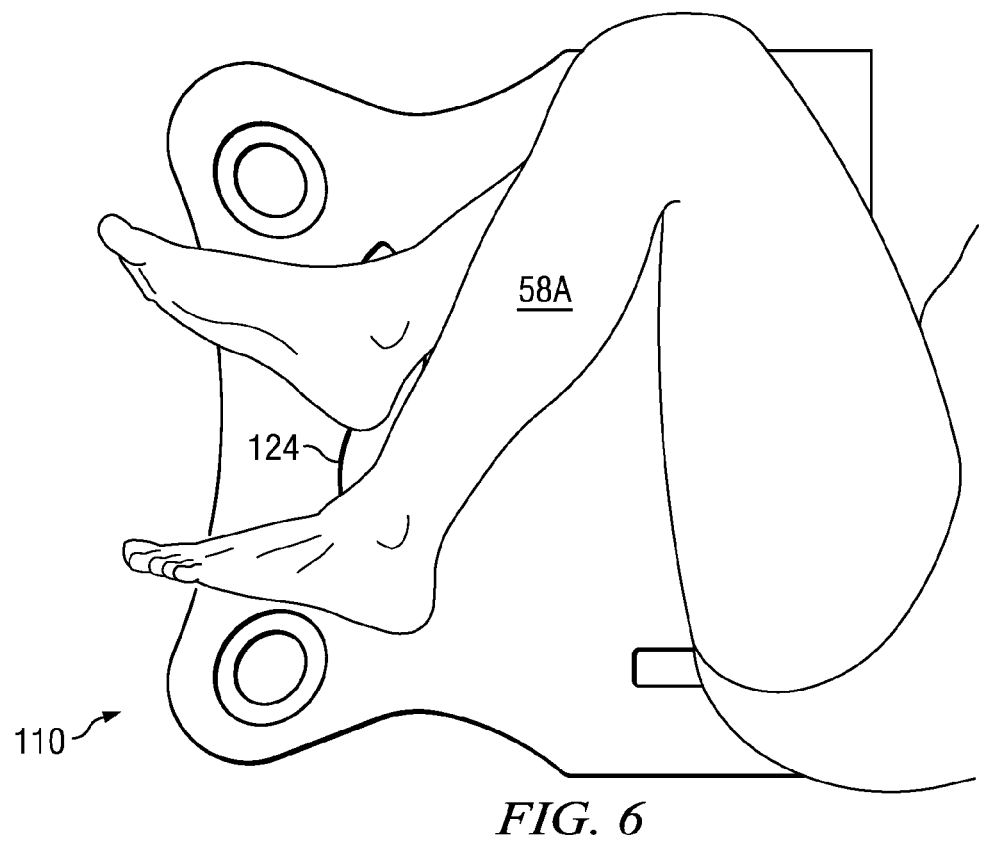
FIG. 6 shows another partial top view of a heel support in a fourth use, namely, wherein the patient is positioned on her right side and her legs are hyper flexed.

FIG. 6 shows another partial top view of a heel support in a fourth use, namely, wherein the patient is positioned on her right side and her legs are hyper flexed or fully flexed. In the embodiment shown in FIG. 6, the central aperture 124 is near the middle of the support to float the bony prominences when the legs are fully flexed or the muscles fully contracted. The aperture 124 is located in the distal region 10 to 17 inches from the proximal (torso end) edge. The aperture preferably is 7 to 10 inches wide and about 2.5 to 4.5 inches long. In this manner, the heel support can serve the patient regardless of her particular body orientation, leg positions, or leg flexure.

The heel support of the present invention may be made from a variety of materials. It should be soft and comfortable for contacting the legs yet firm and structurally solid enough to elevate the legs. In one embodiment the support is made of a material that is water tolerant (and in some embodiments, water resistant) so that it may be washed. In another embodiment the support includes a removable washable cover.

Non-limiting examples of materials for the heel support include foams (such as a polyurethane foam) with a Pounds per cubic foot (PCF) density range of 0.8 to 6.0 and a Indentation Load Deflection (IFD) of 6-36. Additionally, the support may be a composite material or layers. In one embodiment, for example, the top layer is made of a memory foam, preferably a soft and breathable material such as a 3 to 7 pound PCF and an ILD of 6-40. The thickness of the top layer may range from 1 to 2 inches and more preferably is between 0.5 to 1.5 inches and most preferably about 1.5 inch. The bottom layer may be made of a firm material, preferably dense foam. The bottom layer provides structural support and elevation to the top layer and/or patient. PCF and IFD measurements are determined so as to embody the objectives, spirit and scope of the invention.

The body of the support may be made by obtaining a stock or form and cutting or shaping the form to size as is known to those of ordinary skill in the art. Also, certain foams and pads and bodies may be molded, namely, created by an injection molding, casting, or thermo set process. Additionally, sheets of materials may be combined to form composites.

Figure 7:
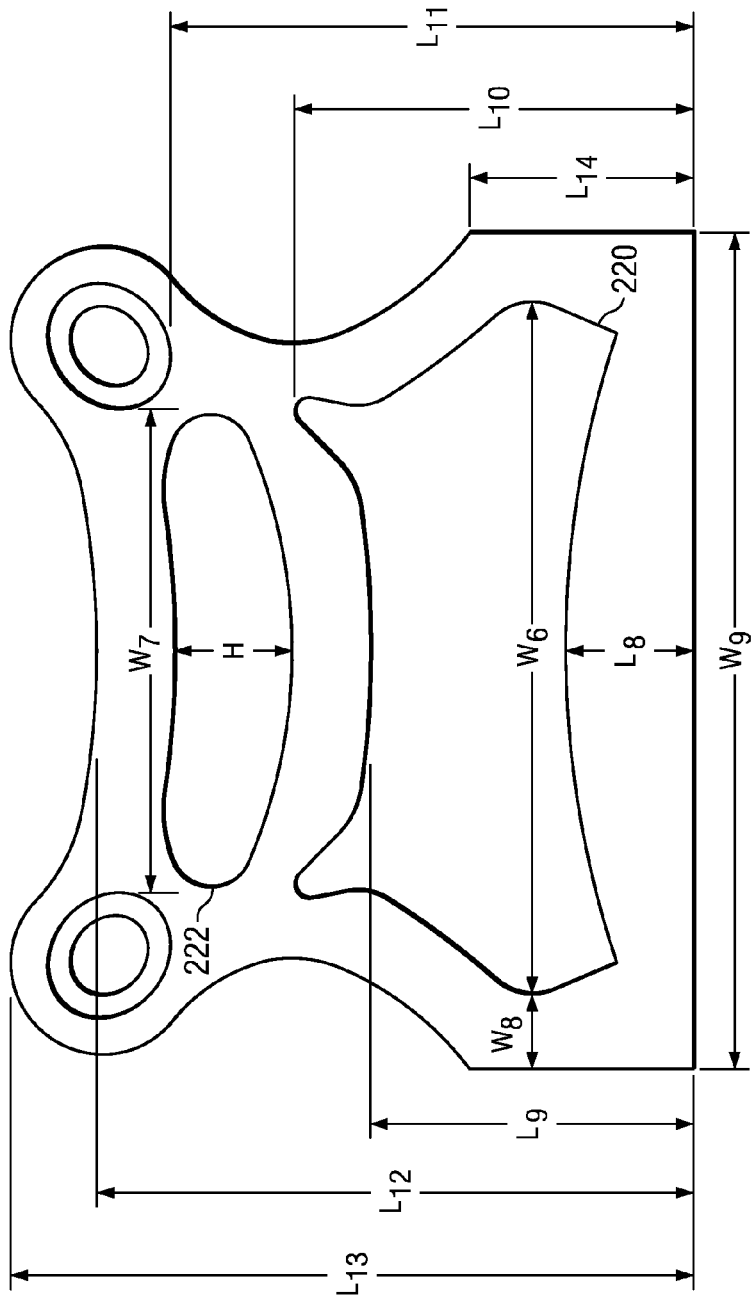
FIG. 7 shows a top view of another heel support in accordance with the present invention.

FIG. 7 shows a top view of another heel support 210 similar to the heel support described above except that it includes a large cavity 220 in the front or proximal region. The cavity 220 serves to provide a short dip under the patient's calves. This dip or cavity distributes the weight or pressure on the legs better than an apparatus without the cavity 220. The presence of cavity 220 provides a softer-feeling support.

The shape and size of the calf cavity 220 may vary. An exemplary shape is shown in FIG. 7 and has a trapezoidal shape. However, other shapes include rectangular, oval, double-oval, or combinations of two, three, or more regions or shapes. The depth may range from approximately 1 to 2 inches or in one embodiment is 1 inch. Alternatively, the cavity may be floorless and extend completely through the heel support.

With reference to FIG. 7, the location of cavity 220 is preferably centered so as to have an axis of symmetry dividing the right and left sides. Non-limiting exemplary dimensions are as follows: H ranges from 2.5-3.5 inches; $L_8$ ranges from 2.5-4 inches; $L_9$ ranges from 7-9 inches; $L_{10}$ ranges from 10-12 inches; $L_{11}$ ranges from 14-16 inches; $L_{12}$ ranges from 15 to 18 inches; $L_{13}$ ranges from 18-22 inches; $L_{14}$ ranges from 4 to 8 inches; $W_6$ ranges from 18-20 inches; $W_7$ ranges from 13-15 inches; $W_8$ ranges from 1.5 to 3.5 inches; and $W_9$ ranges from 20-28 inches.

Additionally, the shape of the central distal aperture 222 is different than that described above. In particular, the central aperture 222 is shown having a crescent or pickle shape. However, the invention is not so limited and the shape of the central aperture may vary.

Figure 8:
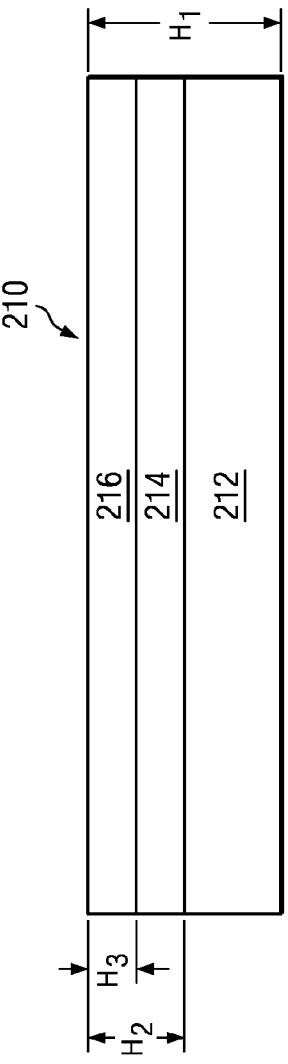
FIG. 8 shows an end view of the heel support shown in FIG. 7.

FIG. 8 shows an end view of the heel support shown in FIG. 7. The heel support 210 is a composite of three layers adhered together. The three layers include bottom support layer 212, intermediate layer 214, and a top layer 216. The bottom layer 212 may be, e.g., a 3 pound foam and preferably has thickness in the range of 1 inch to 2 inches and preferably about 2 inches. The intermediate layer 214 is preferably a 2.5 pound visco elastic, 1-1.5 inch thick foam. The top layer is also preferably a 2.5 pound visco elastic, 1-1.5 inch thick foam.

The calf cavity 220 can be formed by cutting out the shape from the top layer 216. Intermediate layer thus forms a floor to the cavity when the three layers are combined together. The total height $H_1$ of the heel support may vary and may range from 2-4 inches and preferably about 3 inches.

Additionally, the heel support 220 is shown comprising an upper surface which is not sloped. Accordingly, the present invention may have sloped regions, and other embodiments without sloped surfaces.

Additionally, the heel support 220 may comprise a cover (not shown). The cover is preferably sized to snugly fit and conform to the heel support. The cover is preferably removable, soft, and washable. The cover may be by formed of various materials such as, for example, a Nylex fabric, cotton, or another material.

The cover may be attached (e.g., sewn) such that the apertures, cavities and contours remain present and open. In one embodiment, the cover is fastened such that the malleolus apertures and central aperture are open at the upper surface and covered at the bottom. In another embodiment, the calf cavity is covered on both the upper and lower surfaces. Consequently, a wide variety of configurations are possible to cover and uncover the cavities, apertures, and contours as desired.

Although the underlying materials of the heel support in FIGS. 7-8 have been described as composite materials, they need not be. The supportive materials may be molded as described herein and optionally include a cover. Apertures, slopes, cavities, cut-outs etc. may be molded as desired.

Other modifications and variations can be made to the disclosed embodiments without departing from the subject invention. For example, without limitation, the invention may include a first side malleolus aperture and central aperture, a set of side malleolus apertures, a pair of malleolus apertures, a plurality of malleolus apertures for different size, age and types of patient bodies, or any combination thereof.

I claim:

1. A heel support for elevating the heels of a patient from a bed when the patient is positioned on her back and for floating the malleolus when the patient is positioned on her side, said heal support comprising:
   a body comprising an upper surface, a left edge, a right edge being a mirror image of the left edge, and a distal edge, and wherein the distal edge has a center valley such that when the patient is on her back and the heel support is positioned underneath the patient's legs, the center valley acts to maintain the legs of the patient on the support and in the center valley without falling off the heel support and to elevate the heels of the patient from the bed;
   a right side malleolus aperture located in a distal region of the heel support and having a shape, angle and location sufficient to accommodate the lateral malleolus of the patient's right leg when the patient is positioned on her right side and the heel support is positioned underneath the legs of the patient;
   a left side malleolus aperture located in the distal region of the heel support and having a shape, angle and location sufficient to accommodate the medial malleolus of the patient's left leg when the patient is positioned on her right side and the heel support is positioned underneath the legs of the patient and wherein the left edge of the heel support comprises
   a left contour, said left contour comprising a left valley and shaped such that when the patient is on her right side, and the malleolus of the left leg is disposed in the left side malleolus aperture, the heel of the left leg extends off of the left edge and into the left valley of the heel support, thereby floating from the bed; and wherein the right edge of the heel support comprises
   a right contour, said right contour comprising a right valley and shaped such that when the patient is on her left side, and the malleolus of the right leg is disposed in the right side malleolus aperture, the heel of the right leg extends off of the right edge and in the right valley of the heel support, thereby floating from the bed.

2. The heel support of claim 1 further comprising a calf cavity centrally disposed in a proximal region.

3. The heel support of claim 2 wherein the calf cavity comprises a floor.

4. The heel support of claim 1 further comprising a foot end height and a torso end height wherein said foot end height is greater than said torso end height and said foot end height being sufficient to elevate the heel of the patient when the patient is on her back and low enough to allow the heel support to be comfortably positioned underneath the patient's legs when the patient is on her side.

5. The heel support of claim 4 wherein the torso end height is 2.25 inches.

6. The heel support of claim 1 wherein said center valley has a height ranging from 2 to 6 inches.

7. The heel support of claim 6 wherein the center valley is concave.

8. The heel support of claim 1 further comprising a handle.

9. The heel support of claim 1 wherein the body is formed of a plurality of layers including a top layer and wherein the top layer is formed of a memory foam.

10. The heel support of claim 1 wherein the left contour and the right contour are concave.

11. The heel support of claim 1 wherein a proximal region of the heel support is substantially planar and forms an angle with the distal region of the heel support.

12. The heel support of claim 11 wherein said angle ranges from 3 to 7 degrees.

13. The heel support of claim 1 wherein said heel support comprises a length ranging from 15 to 25 inches, and a width ranging from 15 to 25 inches.

14. The heel support of claim 1 wherein each of said left side malleolus aperture and right side malleolus aperture extend said heel support.

15. The heel support of claim 1 further comprising a centrally-located aperture in the distal region of the heel support and for accommodating bony prominences of both feet simultaneously when the patient is positioned on her side.

16. The heel support of claim 15 wherein the centrally-located aperture comprises a width ranging from 7 to 10 inches.

17. The heel support of claim 15 wherein the centrally-located aperture has an oval shape.

* * * * *